United States Patent
Belisle et al.

(10) Patent No.: US 12,364,978 B2
(45) Date of Patent: Jul. 22, 2025

(54) ANIONIC EXCHANGE-HYDROPHOBIC MIXED MODE CHROMATOGRAPHY RESINS

(71) Applicant: BIO-RAD LABORATORIES, INC., Hercules, CA (US)

(72) Inventors: Christopher Belisle, Walnut Creek, CA (US); Xuemei He, Walnut Creek, CA (US); Hong Chen, San Ramon, CA (US); Yueping Xu, Albany, CA (US); Jiali Liao, San Ramon, CA (US)

(73) Assignee: BIO-RAD LABORATORIES, INC., Hercules, CA (US)

( * ) Notice: Subject to any disclaimer, the term of this patent is extended or adjusted under 35 U.S.C. 154(b) by 0 days.

(21) Appl. No.: 18/437,294

(22) Filed: Feb. 9, 2024

(65) Prior Publication Data
US 2024/0261775 A1 Aug. 8, 2024

Related U.S. Application Data

(62) Division of application No. 17/012,108, filed on Sep. 4, 2020, now Pat. No. 11,896,969.

(60) Provisional application No. 62/896,196, filed on Sep. 5, 2019.

(51) Int. Cl.
*B01J 41/14* (2006.01)
*B01J 41/07* (2017.01)
*B01J 47/014* (2017.01)
*B01J 47/02* (2017.01)
*C07K 1/18* (2006.01)
*C12N 9/88* (2006.01)

(52) U.S. Cl.
CPC .............. *B01J 41/14* (2013.01); *B01J 41/07* (2017.01); *B01J 47/014* (2017.01); *B01J 47/02* (2013.01); *C07K 1/18* (2013.01); *C12N 9/88* (2013.01); *C12Y 402/01045* (2013.01); *B01J 2220/52* (2013.01)

(58) Field of Classification Search
None
See application file for complete search history.

(56) References Cited

U.S. PATENT DOCUMENTS

| | | | |
|---|---|---|---|
| 5,429,746 | A | 7/1995 | Shadle et al. |
| 5,645,717 | A | 7/1997 | Hjertén et al. |
| 5,647,979 | A | 7/1997 | Liao et al. |
| 5,652,348 | A | 7/1997 | Burton et al. |
| 5,935,429 | A | 8/1999 | Liao et al. |
| 5,945,520 | A | 8/1999 | Burton et al. |
| 6,423,666 | B1 | 7/2002 | Liao et al. |
| 6,498,236 | B1 | 12/2002 | Lihme et al. |
| 7,714,112 | B2 | 5/2010 | Engstrand et al. |
| 7,867,784 | B2 | 1/2011 | Engstrand et al. |
| 8,748,582 | B2 * | 6/2014 | Hearn ................ B01J 20/3251 530/413 |
| 8,895,710 | B2 | 11/2014 | Engstrand et al. |
| 9,169,331 | B2 | 10/2015 | Liu et al. |
| 9,309,282 | B2 | 4/2016 | Liao et al. |
| 9,486,799 | B2 | 11/2016 | Pohl |
| 9,669,402 | B2 | 6/2017 | Liao et al. |
| 9,975,920 | B2 | 5/2018 | Aldinger et al. |
| 10,287,314 | B2 | 5/2019 | Bian et al. |
| 10,457,749 | B2 | 10/2019 | Fouque et al. |
| 10,487,138 | B2 | 11/2019 | Felföldi et al. |
| 10,682,640 | B2 | 6/2020 | Liao et al. |
| 10,947,268 | B2 | 3/2021 | Li et al. |
| 11,305,271 | B2 | 4/2022 | Yavorsky et al. |
| 11,896,969 | B2 * | 2/2024 | Belisle ................ B01J 20/289 |
| 2006/0052598 | A1 * | 3/2006 | Burton ................ B01J 20/3212 544/198 |
| 2007/0112178 | A1 | 5/2007 | Johansson et al. |
| 2007/0244307 | A1 | 10/2007 | Engstrand et al. |
| 2009/0270596 | A1 | 10/2009 | Gagnon et al. |
| 2011/0139717 | A1 | 6/2011 | Malenfant et al. |
| 2011/0266225 | A1 | 11/2011 | Johansson et al. |
| 2012/0116027 | A1 | 5/2012 | Rasmussen et al. |
| 2012/0259094 | A1 * | 10/2012 | Hearn .................... B01J 20/289 530/413 |
| 2013/0131318 | A1 | 5/2013 | Kremer et al. |
| 2013/0237692 | A1 | 9/2013 | Liao et al. |
| 2013/0289247 | A1 | 10/2013 | Kremer et al. |
| 2015/0073128 | A1 | 3/2015 | Engstrand et al. |
| 2015/0299248 | A1 | 10/2015 | Maloisel et al. |
| 2016/0272673 | A1 | 9/2016 | Althouse et al. |
| 2017/0232433 | A1 * | 8/2017 | Liao ........................ B01J 20/22 521/32 |
| 2017/0334948 | A1 | 11/2017 | Bittermann et al. |
| 2018/0127460 | A1 | 5/2018 | Hall et al. |
| 2018/0154281 | A1 | 6/2018 | Engstrand et al. |

(Continued)

FOREIGN PATENT DOCUMENTS

| | | |
|---|---|---|
| AU | 200173432 | 5/2002 |
| CN | 101060931 | 10/2007 |

(Continued)

OTHER PUBLICATIONS

Written Opinion in International Application No. PCT/US2019/021376, Jul. 9, 2019, pp. 1-7.
International Search Report and Written Opinion in International Application No. PCT/US2020/49305, Feb. 5, 2021, pp. 1-11.
European Search Report for EP 19764738.1, May 7, 2021, pp. 1-13.
Extended European Search Report for EP 19764738.1, Jul. 30, 2021, pp. 1-13.
PubChem ID 26050, "N, N-Dimethyl-2-phenoxyethanamine" Mar. 26, 2005, pp. 1-14.
PubChem CID 37732, Mar. 26, 2005, pp. 1-17.
Abraham; "Solid-Phase Radioimmunoassay of Estradiol-17β"; Preliminary Communications, The Endocrine Society; vol. 29; Jun. 1969; pp. 865-870.
Anspach; "Endotoxin removal by affinity sorbents"; J. Biochem. Biophys. Methods; vol. 49; 2001; pp. 665-681.

(Continued)

*Primary Examiner* — Christian L Fronda
(74) *Attorney, Agent, or Firm* — SALIWANCHIK, LLOYD & EISENSCHENK

(57) ABSTRACT

Chromatography resins having anionic exchange-hydrophobic mixed mode ligands and methods of using such resins are provided.

6 Claims, No Drawings

(56) References Cited

U.S. PATENT DOCUMENTS

| | | | |
|---|---|---|---|
| 2018/0215786 | A1 | 8/2018 | Kozlov et al. |
| 2019/0119415 | A1 | 4/2019 | Graalfs |
| 2020/0406232 | A1 | 12/2020 | Belisle et al. |

FOREIGN PATENT DOCUMENTS

| | | |
|---|---|---|
| CN | 102762585 | 10/2012 |
| CN | 103189390 | 7/2013 |
| CN | 103877748 | 6/2014 |
| CN | 103998456 | 8/2014 |
| CN | 109790201 | 5/2019 |
| WO | WO 90/12632 | 11/1990 |
| WO | WO 97/29825 | 8/1997 |
| WO | WO 2006/043896 | 4/2006 |
| WO | WO 2010/117598 | 10/2010 |
| WO | WO 2011/044637 | 4/2011 |
| WO | WO 2011/104307 | 9/2011 |
| WO | WO 2013/134251 | 9/2013 |
| WO | WO 2019/152977 | 8/2019 |
| WO | WO 2019/173731 | 9/2019 |

OTHER PUBLICATIONS

De Koning et al., "Crosslinked agarose encapsulated sorbents resistant to steam sterilization. Preparation and mechanical properties" Journal of Biomedical Materials Research, vol. 18, 1984, pp. 1-13.

Elder, et al.; "Evaluation of Quaternary Aminoethy-Sephadex A50 Column Chromatography for Detection of Anti-Cytomegalovirus Immunoglobulin M"; Mayo Clin Proc; vol. 62; May 1987; pp. 345-350.

Emöd, et al.; "Five Sepharose-Bound Ligands for the Chromatographic Purification of Clostridium Collagenase and Clostripain"; FEBS Letters; vol. 77, No. 1; May 1977; pp. 51-56.

Eriksson. K. et al. "MAb Contaminant Removal with a Multimodal Anion Exchanger A Platform Step to Follow Protein A" BioProcess International, Feb. 2009, pp. 52-56, vol. 7, No. 2.

Franek; "Purification of IgG Monocloanl Antibodies from Ascitic Fluid Based on Rivanol Precipitation"; Methods in Enzymology; vol. 121; 1986; 631-638.

Fung, et al.; "Serologic Diagnosis of Toxoplasmosis with Emphasis on the Detection of Toxoplasma-specific Immunoglobulin M Antibodies"; American Journal of Clinical Pathology; vol. 83, No. 2; Feb. 1983; pp. 196-199.

Horejsi, et al.; "The Isolation of Gamma Globulin from Blood-Serum by Rivanol"; Acta Medica Scandinavica; vol. CLV, fasc. I; submitted for publication Mar. 27, 1956; pp. 65-70.

Jaber, et al.; "Extracorporeal Adsorbent-Based Strategies in Sepsis"; American J of Kidney Diseases; vol. 30, No. 5, Suppl 4; Nov. 1997; pp. S44-S56.

Jelezarova, et al.; "Interaction of C3b2-IgG complexes with complement proteins properdin, factor B and factor H: implications for amplification"; Biochem J.; vol. 349; 2000; pp. 217-223.

Joustra, et al.; "Preparation of Freeze-dried, Monomeric and Immunochemically Pure IgG by a Rapid and Reproducible Chromatographic Technique"; from Protides of the Biological Fluids, Chapter D: Techniques; Published by Elsevier; vol. 17, 1970, pp. 510-515.

Li, Y. et al. "New reversed-phase/anion-exchange/hydrophilic interaction mixed-mode stationary phase based on dendritic polymer-modified porous silica" Journal of Chromatography A, 2014, pp. 133-139, vol. 1337.

Nemoto, et al.; "Newly Developed Immobilized Polymyxin B Fibers Improve the Survival of Patients with Sepsis"; Blood Purif.; vol. 19; 2001; pp. 361-369.

Mayer, et al.; "Modifying an immunogenic epitope on a therapeutic protein: a step towards an improved system for antibody-directed enzyme prodrug therapy (ADEPT)"; British J. of Cancer; vol. 90; May 25, 2004; pp. 2402-2410.

Miller; "Rivanol, Resin and the Isolation of Thrombins"; Nature; vol. 184; Aug. 8, 1959; p. 450.

Persson, et al.; "Purification of Antibody and Antibody-Fragment From E. coli Homogenate Using 6,9-Diamino-2-ethoxyacridine Lactate as Precipitation Agent"; Biotechnology and Bioengineering; vol. 87, No. 3, Aug. 5, 2004; pp. 424-434.

Petsch, et al.; "Endotoxin removal from protein solutions"; J. of Biotechnology; vol. 76; 2000; pp. 97-119.

Sato, et al.; "Development of Mammalian Serum Albumin Affinity Purification Media by Peptide Phage Display"; Biotechnol. Prog. vol 18; Jan. 26, 2002; pp. 182-192.

Simmons, et al.; "Expression of full-length immunoglobulins in Escherichia coli: rapid and efficient production of aglycosylated antibodies"; J. of Immunological Methods; vol. 263; Feb. 14, 2002; pp. 133-147.

Talmadge, et al.; "Efficient Endotoxin Removal with a New Sanitizable Affinity Column; Affi-Prep Polymyxin"; J. of Chromatography; vol. 476; 1989; pp. 175-185.

Te Booy, et al.; "Affinity purification of plasma proteins: characterization of six affinity matrices and their application for the isolation of human factor VIII"; Thromb. Haemost.; vol. 61(2); Apr. 1989; pp. 234-237.

Te Booy, et al.; "Large-scale purification of factor VIII by affinity chromatography: optimization of process parameters"; J. of Chromatography; vol. 503; 1990; pp. 103-114.

\* cited by examiner

ANIONIC EXCHANGE-HYDROPHOBIC MIXED MODE CHROMATOGRAPHY RESINS

This application is a divisional of U.S. application Ser. No. 17/012,108, filed Sep. 4, 2020, now U.S. Pat. No. 11,896,969, which claims the benefit of U.S. Provisional Application 62/896,196 filed on Sep. 5, 2019 which is hereby incorporated by reference in its entirety.

BACKGROUND

The extraction of immunoglobulins from source liquids, which are primarily mammalian bodily fluids or cell culture harvest, is of value in obtaining the immunoglobulins in a sufficiently concentrated or purified form for diagnostic and therapeutic uses as well as laboratory studies in general. Similarly, purification of other types of proteins and other molecules from biological samples can be of value.

SUMMARY

Chromatography resins comprising chromatography matrices linked to an anionic exchange-hydrophobic mixed mode ligand are provided. In some embodiments, the chromatography resin has the formula:

$$\text{Chromatography matrix-}(X)\text{—}N(R^1)\text{—}(R^2\text{—}L)_n\text{—}Ar$$

or an anionic salt thereof,
wherein
  X is a spacer;
  $R^1$ is hydrogen or $C_1$ to $C_6$ alkyl optionally substituted with an —OH;
  $R^2$ is $C_2$ to $C_6$ alkyl or $C_4$ to $C_6$ cycloalkyl;
  L is $NR^4$, O, or S;
  n=1 or 2; and
  Ar is a 6-10 membered ring and:
    if Ar is aryl, the aryl is optionally substituted with up to five $C_1$ to $C_3$ unsubstituted alkyl, $C_3$ to $C_6$ branched alkyl, unsubstituted aryl, or fluorine groups; or
    if Ar is heteroaryl, the heteroaryl is optionally substituted with up to four unsubstituted alkyl groups,
  with the proviso that when $R^1$ is hydrogen, $R^2$ is $C_2$ alkyl, L is $NR^4$ or O, and n is 1, Ar is not phenyl.
In some embodiments of the chromatography resin:
X is selected from the group consisting of —O—$CH_2$—, —O—$CH_2$—$CH_2$—, —O—$CH_2$—$CH_2$—$CH_2$—, —O—$CH_2$—$CH_2$—$CH_2$—$CH_2$—, —O—$CH_2$—CH($CH_2$—OH)—(O—$CH_2$—CH(OH)—$CH_2$)$_2$—, —O—$CH_2$—$CH_2$—CH($CH_2$—OH)—(O—$CH_2$—$CH_2$—CH(OH)—$CH_2$)$_2$—, —O—$CH_2$—CH(OH)—$CH_2$—, —O—$CH_2$—$CH_2$—CH(OH)—$CH_2$—$CH_2$—, —O—$CH_2$—CH(OH)—$CH_2$—O—$CH_2$—$CH_2$—$CH_2$—$CH_2$—O—$CH_2$—CH(OH)—$CH_2$—, and —CO—NH—C($CH_3$)$_2$—CO—;
$R^1$ is hydrogen or $C_1$ to $C_3$ alkyl;
$R^2$ is $C_2$ to $C_4$ alkyl;
L is O;
n=1; and
Ar is a 6 membered ring and:
  if Ar is aryl, the aryl is optionally substituted with up to four $C_1$ to $C_2$ unsubstituted alkyl, $C_3$ or $C_4$ branched alkyl, or fluorine groups; or
  if Ar is heteroaryl, the heteroaryl is optionally substituted with up to three unsubstituted alkyl groups,
  with the proviso that when $R^1$ is hydrogen, $R^2$ is $C_2$ alkyl, and n is 1, Ar is not phenyl.

DETAILED DESCRIPTION

Provided are chromatography resins that are useful for purifying target biomolecules using anionic exchange and hydrophobic mixed mode chromatography. The chromatography resins allow for efficient purification of target biomolecules (e.g., recombinant proteins) from a sample. In an embodiment, the chromatography resins are useful for separating a target protein from one or more components (e.g., contaminants) in the sample.

Definitions

Unless otherwise stated, the following terms used in this application, including the specification and claims, have the definitions given below. As used in this specification and the appended claims, the singular forms "a", "an", and "the" include plural referents unless the content clearly dictates otherwise. Definition of standard chemistry terms can be found in reference works, including Carey and Sundberg (2007) "Advanced Organic Chemistry 5th Ed." Vols. A and B, Springer Science+Business Media LLC, New York. The practice of the present invention will employ, unless otherwise indicated, conventional methods of synthetic organic chemistry, mass spectroscopy, preparative and analytical methods of chromatography, protein chemistry, biochemistry, recombinant DNA techniques and pharmacology.

As used herein, the term "alkyl" refers to a straight or branched, saturated, aliphatic radical having between 1-10 carbon atoms. For example, $C_1$-$C_6$ alkyl includes, but is not limited to, methyl, ethyl, propyl, isopropyl, butyl, isobutyl, sec-butyl, tert-butyl, pentyl, isopentyl, and/or hexyl. Alkyl can include any number of carbons, such as 1-2, 1-3, 1-4, 1-5, 1-6, 1-7, 1-8, 1-9, 1-10, 2-3, 2-4, 2-5, 2-6, 3-4, 3-5, 3-6, 4-5, 4-6 and 5-6. The alkyl group is typically monovalent, but can be divalent, such as when the alkyl group links two chemical groups together.

As used herein, the term "cycloalkyl" refers to monocyclic alkyl having the number of carbon atoms indicated. Monocyclic rings include, for example, cyclopropyl, cyclobutyl, cyclopentyl, and cyclohexyl.

As used herein, the term "aryl" refers to a monocyclic or fused bicyclic aromatic ring assembly. For example, aryl can be phenyl, or naphthyl. Aryl groups can optionally be substituted by one, two, three, four, or five unsubstituted alkyl groups, unsubstituted aryl groups, or fluorine groups.

The term "heteroatom" refers to N, O and S.

As used herein, the term "heteroaryl group" refers to aromatic groups that include one heteroatom as a ring member. Examples include, but are not limited to, pyrrole, furan, thiophene, and pyridine. Heteroaryl groups can optionally be substituted by one, two, three, or four alkyl groups.

An "anionic salt" is formed at a basic (e.g., amino or alkylamino) group in the ligands. Anionic salts include, but are not limited to, halides, sulfonates, sulfates, carboxylates, phosphates, acetates, citrates and nitrates. Examples of acid-addition salts include, but are not limited to, hydrochloride, hydrobromide, hydroiodide, sulfate, acetate, citrate, and nitrate.

As used herein, the term "spacer" refers to a molecule having 1-30 atoms selected from H, C, N, O and S. The spacer has a neutral charge and can include cyclic groups. The spacer links the chromatographic ligand to the chromatography matrix. The types of bonds used to link the spacer to the chromatography matrix include, but are not limited to, amides, amines, ethers, esters, carbamates, ureas, thioethers, thiocarbamates, thiocarbonate and thioureas. In some embodiments, the bonds used to link the spacer to the chromatography matrix are amines, ethers or amides.

"Biological sample" refers to any composition containing a target molecule of biological origin (a "biomolecule") that is desired to be purified. In some embodiments, the target molecule to be purified is an antibody or a non-antibody protein.

"Antibody" refers to an immunoglobulin, composite (e.g., fusion), or fragmentary form thereof. The term includes but is not limited to polyclonal or monoclonal antibodies of the classes IgA, IgD, IgE, IgG, and IgM, derived from human or other mammalian cell lines, including natural or genetically modified forms such as humanized, human, single-chain, chimeric, synthetic, recombinant, hybrid, mutated, grafted, and in vitro generated antibodies. "Antibody" also includes composite forms including but not limited to fusion proteins containing an immunoglobulin moiety. "Antibody" also includes antibody fragments such as Fab, F(ab')$_2$, Fv, scFv, Fd, dAb, Fc, whether or not they retain antigen-binding function.

The term "protein" refers to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers (e.g., recombinant proteins).

"Bind-elute mode" refers to an operational approach to chromatography in which the buffer conditions are established so that target molecules and, optionally undesired contaminants, bind to the ligand when the sample is applied to the ligand. Fractionation of the target can be achieved subsequently by changing the conditions such that the target is eluted from the support. In some embodiments, contaminants remain bound following target elution. In some embodiments, contaminants either flow-through or are bound and eluted before elution of the target.

"Flow-through mode" refers to an operational approach to chromatography in which the buffer conditions are established so that the target molecule to be purified flows through the chromatography support comprising the ligand, while at least some sample contaminants are selectively retained, thus achieving their removal from the sample.

Chromatography Ligands

In an embodiment, a mixed mode chromatography support and ligand has the formula:

$$\text{Chromatography matrix-}(X)\text{---}N(R^1)\text{---}(R^2\text{---}L)_n\text{---}Ar$$

or anionic salt thereof,
wherein:
  X is a spacer;
  $R^1$ is hydrogen or $C_1$ to $C_6$ alkyl optionally substituted with an —OH;
  $R^2$ is $C_2$ to $C_6$ alkyl or $C_4$ to $C_6$ cycloalkyl;
  L is $NR^4$, O, or S;
  n=1 or 2; and
  Ar is a 6-10 membered ring and:
    if Ar is aryl, the aryl is optionally substituted with up to five $C_1$ to $C_3$ unsubstituted alkyl, $C_3$ to $C_6$ branched alkyl, unsubstituted aryl, or fluorine groups; or
    if Ar is heteroaryl, the heteroaryl is optionally substituted with up to four unsubstituted alkyl groups, with the proviso that when $R^1$ is hydrogen, $R^2$ is $C_2$ alkyl, L is $NR^4$ or O, and n is 1, Ar is not phenyl.

The charge of the nitrogen adjacent to the spacer is dependent on pH. Therefore these resins provide weak ion exchange.

In a first aspect of the first embodiment, $R^1$ is hydrogen or $C_1$ to $C_3$ alkyl. Alternatively, $R^1$ is hydrogen or $C_1$ to $C_2$ alkyl.

In a second aspect of the first embodiment, $R^2$ is $C_2$ to $C_4$ alkyl. Alternatively, $R^2$ is $C_2$ or $C_3$ alkyl.

In a third aspect of the first embodiment, L is $NR^4$ or O; or $NR^4$ or S. Alternatively, L is O.

In a fourth aspect of the first embodiment, n is 1.

In a fifth aspect of the first embodiment, Ar is a 6 membered ring and if Ar is aryl, the aryl is optionally substituted with up to four $C_1$ to $C_2$ unsubstituted alkyl, $C_3$ to $C_4$ branched alkyl, or fluorine groups or if Ar is heteroaryl, the heteroaryl is optionally substituted with up to three alkyl groups, with the proviso that when $R^1$ is hydrogen, $R^2$ is $C_2$ alkyl, L is $NR^4$ or O, and n is 1, Ar is not phenyl. Alternatively, Ar is phenyl, napthyl, or pyridyl optionally substituted with up to three $C_1$ to $C_2$ unsubstituted alkyl or fluorine groups, with the proviso that when $R^1$ is hydrogen, $R^2$ is $C_2$ alkyl, L is $NR^4$ or O, and n is 1, Ar is not phenyl. Alternatively, Ar is phenyl optionally substituted with one or two $C_1$ to $C_2$ unsubstituted alkyl, with the proviso that when $R^1$ is hydrogen, $R^2$ is $C_2$ alkyl, L is $NR^4$ or O, and n is 1, Ar is not phenyl. Alternatively, Ar is phenyl substituted with one $C_1$ to $C_3$ unsubstituted alkyl, $C_3$ to $C_6$ branched alkyl, unsubstituted aryl, or fluorine groups at the para or meta position relative to Chromatography matrix —(X)—N($R^1$)—($R^2$-L)$_n$-. Alternatively, Ar is heteroaryl and a heteroatom in the heteroaryl is N. Alternatively, Ar is unsubstituted heteroaryl. In yet another alternative, Ar is pyridyl.

In a sixth aspect of the first embodiment, X is attached to chromatography matrix via a bond selected from an amide, amine, ether, ester, carbamate, urea, thioether, thiocarbamate, thiocarbonate and thiourea. Alternatively the bond is an amine, ether or amide.

In an seventh aspect of the first embodiment, X is selected from the group consisting of —O—$CH_2$—, —O—$CH_2$—$CH_2$—, —O—$CH_2$—$CH_2$—$CH_2$—, —O—$CH_2$—$CH_2$—$CH_2$—$CH_2$—, —O—$CH_2$—CH($CH_2$—OH)—(O—$CH_2$—CH(OH)—$CH_2$)$_2$—, —O—$CH_2$—$CH_2$—CH($CH_2$—OH)—(O—$CH_2$—$CH_2$—CH(OH)—$CH_2$)$_2$—, —O—$CH_2$—CH(OH)—$CH_2$—, —O—$CH_2$—$CH_2$—CH(OH)—$CH_2$—$CH_2$—, —O—$CH_2$—CH(OH)—$CH_2$—O—$CH_2$—$CH_2$—$CH_2$—$CH_2$—O—$CH_2$—CH(OH)—$CH_2$—, and —CO—NH—C($CH_3$)$_2$—CO—. Alternatively, X is selected from the group consisting of —O—$CH_2$—, —O—$CH_2$—$CH_2$—, —O—$CH_2$—$CH_2$—$CH_2$—, —O—$CH_2$—$CH_2$—$CH_2$—$CH_2$—, and —O—$CH_2$—CH(OH)—$CH_2$—.

In a second embodiment, the chromatography resin has the formula:

$$\text{Chromatography matrix-}(X)\text{---}N(R^1)\text{---}(R^2\text{---}L)_n\text{---}Ar$$

or an anionic salt thereof, wherein:
X is selected from the group consisting of —O—CH$_2$—, —O—CH$_2$—CH$_2$—, —O—CH$_2$—CH$_2$—CH$_2$—, —O—CH$_2$—CH$_2$—CH$_2$—CH$_2$—, —O—CH$_2$—CH(CH$_2$—OH)—(O—CH$_2$—CH(OH)—CH$_2$)$_2$—, —O—CH$_2$—CH$_2$—CH(CH$_2$—OH)—(O—CH$_2$—CH$_2$—CH(OH)—CH$_2$)$_2$—, —O—CH$_2$—CH(OH)—CH$_2$—, —O—CH$_2$—CH$_2$—CH(OH)—CH$_2$—CH$_2$—, —O—CH$_2$—CH(OH)—CH$_2$—O—CH$_2$—CH$_2$—CH$_2$—CH$_2$—O—CH$_2$—CH(OH)—CH$_2$—, and —CO—NH—C(CH$_3$)$_2$—CO—;
R$^1$ is hydrogen or C$_1$ to C$_3$ alkyl;
R$^2$ is C$_2$ to C$_4$ alkyl;
L is O;
n=1; and
Ar is a 6 membered ring and:
 if Ar is aryl, the aryl is optionally substituted with up to four C$_1$ to C$_2$ unsubstituted alkyl, C$_3$ or C$_4$ branched alkyl, or fluorine groups; or
 if Ar is heteroaryl, the heteroaryl is optionally substituted with up to three unsubstituted alkyl groups,
 with the proviso that when R$^1$ is hydrogen, R$^2$ is C$_2$ alkyl, and n is 1, Ar is not unsubstituted phenyl.

In a first aspect of the second embodiment, R$^1$ is hydrogen or C$_1$ to C$_2$ alkyl.

In a second aspect of the second embodiment, R$^2$ is C$_2$ or C$_3$ alkyl.

In a third aspect of the second embodiment, Ar is phenyl, napthyl, or pyridyl optionally substituted with up to three C$_1$ to C$_2$ unsubstituted alkyl or fluorine groups, with the proviso that when R$^1$ is hydrogen, R$^2$ is C$_2$ alkyl, L is NR$^4$ or O, and n is 1, Ar is not phenyl. Alternatively, Ar is phenyl optionally substituted with one or two C$_1$ to C$_2$ unsubstituted alkyl, with the proviso that when R$^1$ is hydrogen, R$^2$ is C$_2$ alkyl, L is NR$^4$ or O, and n is 1, Ar is not phenyl. Alternatively, Ar is phenyl substituted with one C$_1$ to C$_2$ unsubstituted alkyl at the para or meta position relative to Chromatography matrix —(X)—N(R$^1$)—(R$^2$-L)$_n$-. Alternatively, Ar is heteroaryl and a heteroatom in the heteroaryl is N. Alternatively, Ar is unsubstituted heteroaryl. In yet another alternative, Ar is pyridyl.

In a third embodiment, the chromatography resin has the formula:

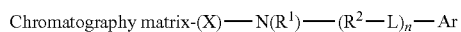

Chromatography matrix-(X)—N(R$^1$)—(R$^2$—L)$_n$—Ar or an anionic salt thereof,
wherein:
X is selected from the group consisting of —O—CH$_2$—, —O—CH$_2$—CH$_2$—, —O—CH$_2$—CH$_2$—CH$_2$—, —O—CH$_2$—CH$_2$—CH$_2$—CH$_2$—, and —O—CH$_2$—CH(OH)—CH$_2$—;
R$^1$ is hydrogen or C$_1$ to C$_2$ alkyl;
R$^2$ is C$_2$ to C$_3$ alkyl;
L is O;
n=1; and
Ar is phenyl, napthyl, or pyridyl optionally substituted with up to three C$_1$ to C$_2$ unsubstituted alkyl,
 with the proviso that when R$^1$ is hydrogen, R$^2$ is C$_2$ alkyl, and n is 1, Ar is not unsubstituted phenyl.

In a first aspect of the third embodiment, Ar is phenyl optionally substituted with one or two C$_1$ to C$_2$ unsubstituted alkyl, with the proviso that when R$^1$ is hydrogen, R$^2$ is C$_2$ alkyl, Ar is not phenyl. Alternatively, Ar is phenyl substituted with a methyl group at the para or meta position relative to Chromatography matrix —(X)—N(R$^1$)—(R$^2$-L)$_n$-. Alternatively, Ar is unsubstituted phenyl with the proviso that R$^1$ is not hydrogen, R$^2$ is not C$_2$ alkyl.

In a fourth embodiment, —(X)—N(R$^1$)—(R$^2$-L)$_n$-Ar is any one of the ligands of Table 1.

TABLE 1

| Number | Ligand | Structure of Ligand | Structure of Ligand Attached to Matrix (Spheres represent matrix and Spacer X) |
|---|---|---|---|
| 1 | 2-(p-Tolyloxy)ethylamine | | |
| 2 | 2-(o-Tolyloxy)ethylamine | | |
| 3 | 2-(m-Tolyloxy)ethylamine | | |

TABLE 1-continued

| Number | Ligand | Structure of Ligand | Structure of Ligand Attached to Matrix (Spheres represent matrix and Spacer X) |
|---|---|---|---|
| 4 | 3,5-dimethylphenoxy-ethanamine | | |
| 5 | 4-ethylphenoxy ethanamine | | |
| 6 | 4-isopropylphenoxy ethanamine | | |
| 7 | 4-t-butylphenoxy ethanamine | | |
| 8 | 4-phenylphenoxy ethanamine | | |
| 9 | 1-naphthalenoxy ethanamine | | |
| 10 | 3-flourophenoxy ethanamine | | |
| 11 | 4-flourophenoxy ethanamine | | |

TABLE 1-continued

| Number | Ligand | Structure of Ligand | Structure of Ligand Attached to Matrix (Spheres represent matrix and Spacer X) |
|---|---|---|---|
| 12 | 3,5-diflourophenoxy ethanamine | | |
| 13 | 2,5-diflourophenoxy ethanamine | | |
| 14 | 3,4-diflourophenoxy ethanamine | | |
| 15 | 3,4,5-triflourophenoxy ethanamine | | |
| 16 | perflourophenoxy ethanamine | | |
| 17 | 4-pyridinylethanamine | | |
| 18 | 3-pyridinylethanamine | | |
| 19 | 4-(2,6-dimethylpyridinyl) ethanamine | | |

TABLE 1-continued

| Number | Ligand | Structure of Ligand | Structure of Ligand Attached to Matrix (Spheres represent matrix and Spacer X) |
|---|---|---|---|
| 20 | Phenoxypropylamine | | |
| 21 | 2-Phenoxycyclobutyl-amine | | |
| 22 | 2-Phenoxycyclopentyl amine | | |
| 23 | 4-Phenoxycyclohexyl-amine | | |
| 24 | 2-(2-phenoxyethoxy) ethanamine | | |
| 25 | N-methyl-2-phenoxyethan-1-amine | | |
| 26 | N-methyl-3-phenoxypropan-1-amine | | |
| 27 | N-methyl(2-phenoxy cyclobutyl)amine | | |
| 28 | N-methyl(2-phenoxy cyclopentyl)amine | | |
| 29 | N-methyl(4-phenoxy cyclohexyl)amine | | |

TABLE 1-continued

| Number | Ligand | Structure of Ligand | Structure of Ligand Attached to Matrix (Spheres represent matrix and Spacer X) |
|---|---|---|---|
| 30 | N-methyl-2-(p-tolyloxy)ethan-1-amine | 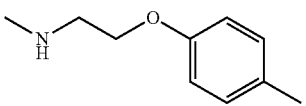 | 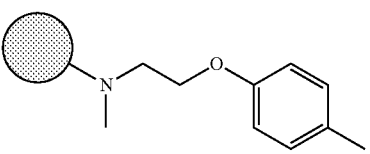 |
| 31 | 2-(3,5-dimethylphenoxy)-N-methylethan-1-amine | 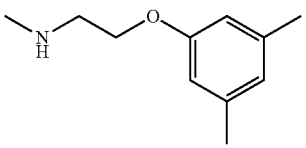 | 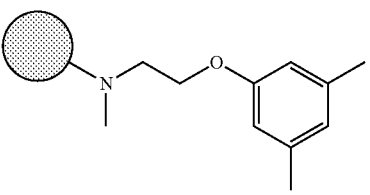 |
| 32 | 2-(4-ethylphenoxy)-N-methylethan-1-amine | 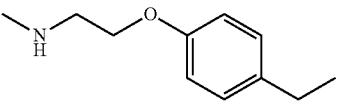 | 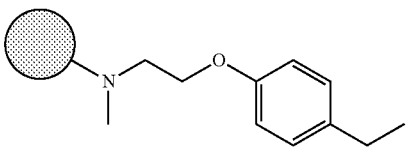 |
| 33 | 2-(4-isopropylphenoxy)-N-methylethan-1-amine | 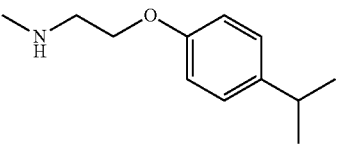 | 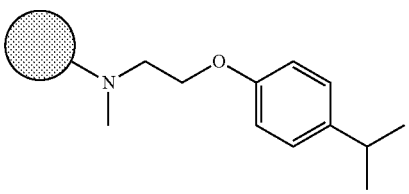 |
| 34 | 2-(4-(tert-butyl)phenoxy)-N-methylethan-1-amine | 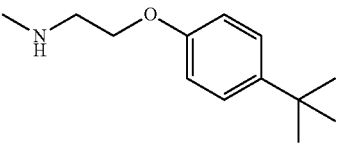 | 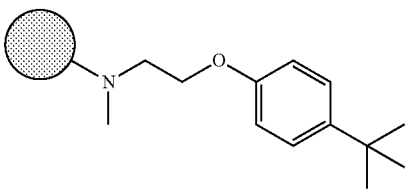 [SMILES: CN(C)CCOc1ccc(C(C)(C)C)cc1] |
| 35 | 2-([1,1'-biphenyl]-4-yloxy)-N-methylethan-1-amine | 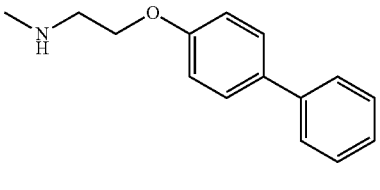 [SMILES: CNCCOc1ccc(-c2ccccc2)cc1] | 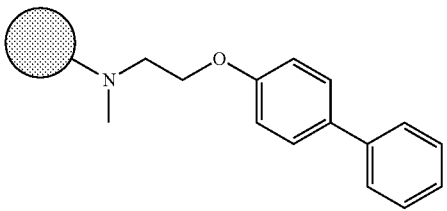 [SMILES: CN(C)CCOc1ccc(-c2ccccc2)cc1] |
| 36 | N-methyl-2-(naphthalen-1-yloxy)ethan-1-amine | 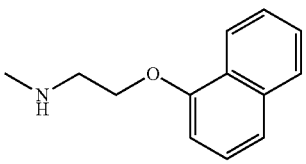 | 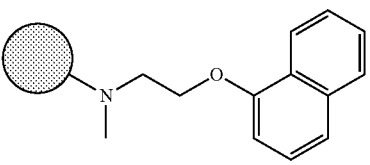 [SMILES: CN(C)CCOc1cccc2ccccc12] |
| 37 | 2-((2-phenoxyethyl)amino)ethan-1-ol | 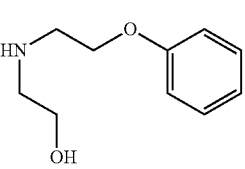 | 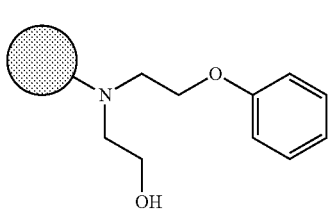 |

TABLE 1-continued

| Number | Ligand | Structure of Ligand | Structure of Ligand Attached to Matrix (Spheres represent matrix and Spacer X) |
|---|---|---|---|
| 38 | 2-(3-fluorophenoxy)-N-methylethan-1-amine | 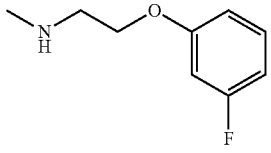 | 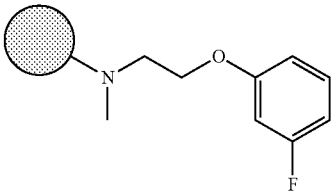 |
| 39 | 2-(4-fluorophenoxy)-N-methylethan-1-amine | 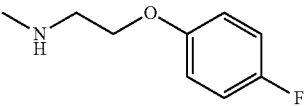 | 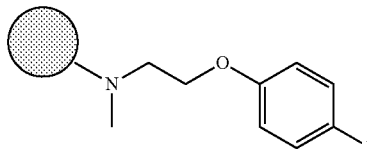 |
| 40 | 2-(2,5-difluorophenoxy)-N-methylethan-1-amine | 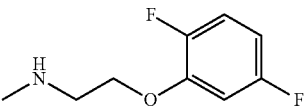 | 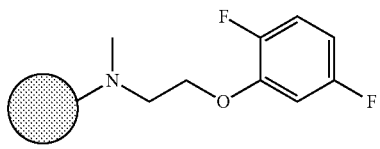 |
| 41 | 2-(3,4-difluorophenoxy)-N-methylethan-1-amine | 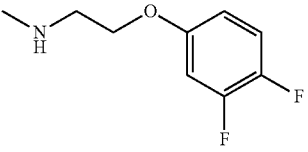 | 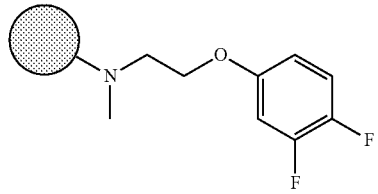 |
| 42 | 2-(3,5-difluorophenoxy)-N-methylethan-1-amine | 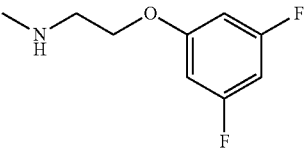 | 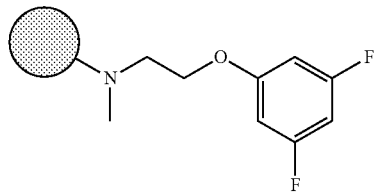 |
| 43 | N-methyl-2-(3,4,5-trifluorophenoxy)ethan-1-amine | 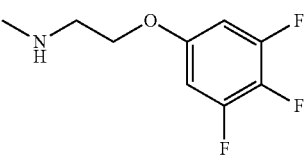 | 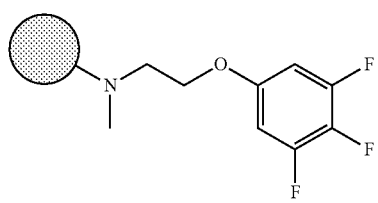 |
| 44 | N-methyl-2-(perfluorophenoxy)ethan-1-amine | 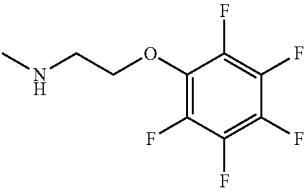 [SMILES: CNCCOc1c(F)c(F)c(F)c(F)c1F] | 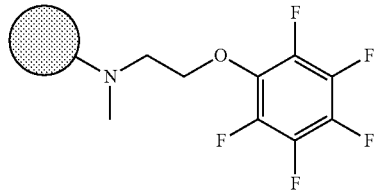 |
| 45 | N-methyl-2-(pyridin-4-yloxy)ethan-1-amine | 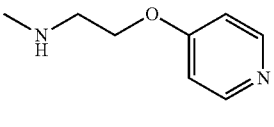 | 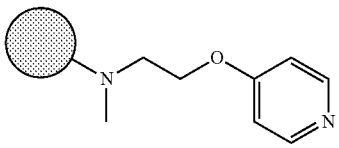 |

TABLE 1-continued

| Number | Ligand | Structure of Ligand | Structure of Ligand Attached to Matrix (Spheres represent matrix and Spacer X) |
|---|---|---|---|
| 46 | N-methyl-2-(pyridin-3-yloxy)ethan-1-amine | 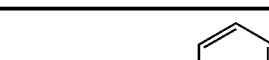 | 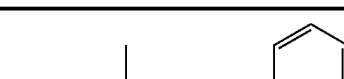 |
| 47 | 2-((2,6-dimethylpyridin-4-yl)oxy)-N-methylethan-1-amine |  |  |
| 48 | N-methyl-2-(2-phenoxyethoxy)ethan-1-amine | 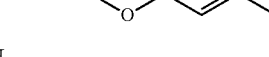 | 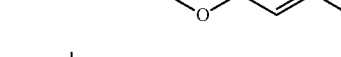 |

In a fifth embodiment, the chromatography resin has the formula:

$$\text{Chromatography matrix-(X)}-N-[(R^2-L)_n-Ar]_2$$

or an anionic salt thereof,
wherein:
X is a spacer;
$R^2$ is $C_2$ to $C_6$ alkyl or $C_4$ to $C_6$ cycloalkyl;
L is $NR^4$, O, or S;
n=1 or 2; and
Ar is a 6-10 membered ring and:
  if Ar is aryl, the aryl is optionally substituted with up to five $C_1$ to $C_3$ unsubstituted alkyl, $C_3$ to $C_6$ branched alkyl, unsubstituted aryl, or fluorine groups; or
  if Ar is heteroaryl, the heteroaryl is optionally substituted with up to four unsubstituted alkyl groups.

In a first aspect of the fifth embodiment, $R^2$ is $C_2$ to $C_4$ alkyl. Alternatively, $R^2$ is $C_2$ or $C_3$ alkyl.

In a second aspect of the fifth embodiment, L is $NR^4$ or O; or $NR^4$ or S. Alternatively, L is O.

In a third aspect of the fifth embodiment, n is 1.

In a fourth aspect of the fifth embodiment, Ar is a 6 membered ring and if Ar is aryl, the aryl is optionally substituted with up to four $C_1$ to $C_2$ unsubstituted alkyl, $C_3$ to $C_4$ branched alkyl, or fluorine groups or if Ar is heteroaryl, the heteroaryl is optionally substituted with up to three alkyl groups. Alternatively, Ar is phenyl, napthyl, or pyridyl optionally substituted with up to three $C_1$ to $C_2$ unsubstituted alkyl or fluorine groups. Alternatively, Ar is phenyl optionally substituted with one or two $C_1$ to $C_2$ unsubstituted alkyl. Alternatively, Ar is phenyl substituted with one $C_1$ to $C_3$ unsubstituted alkyl, $C_3$ to $C_6$ branched alkyl, unsubstituted aryl, or fluorine groups at the para or meta position relative to $-(R^2-L)_n-$. Alternatively, Ar is heteroaryl and a heteroatom in the heteroaryl is N. Alternatively, Ar is unsubstituted heteroaryl. In yet another alternative, Ar is pyridyl.

In a fifth aspect of the fifth embodiment, X is attached to chromatography matrix via a bond selected from an amide, amine, ether, ester, carbamate, urea, thioether, thiocarbamate, thiocarbonate and thiourea. Alternatively the bond is an amine, ether or amide.

In an sixth aspect of the fifth embodiment, X is selected from the group consisting of $-O-CH_2-$, $-O-CH_2-CH_2-$, $-O-CH_2-CH_2-CH_2-$, $-O-CH_2-CH_2-CH_2-CH_2-$, $-O-CH_2-CH(CH_2-OH)-(O-CH_2-CH(OH)-CH_2)_2-$, $-O-CH_2-CH_2-CH(CH_2-OH)-(O-CH_2-CH_2-CH(OH)-CH_2)_2-$, $-O-CH_2-CH(OH)-CH_2-$, $-O-CH_2-CH_2-CH(OH)-CH_2-CH_2-$, $-O-CH_2-CH(OH)-CH_2-O-CH_2-CH_2-CH_2-CH_2-O-CH_2-CH(OH)-CH_2-$, and $-CO-NH-C(CH_3)_2-CO-$. Alternatively, X is selected from the group consisting of $-O-CH_2-$, $-O-CH_2-CH_2-$, $-O-CH_2-CH_2-CH_2-$, $-O-CH_2-CH_2-CH_2-CH_2-$, and $-O-CH_2-CH(OH)-CH_2-$.

In a sixth embodiment, the chromatography resin has the formula:

$$\text{Chromatography matrix-(X)}-N-[(R^2-L)_n-Ar]_2$$

or an anionic salt thereof,
wherein:
X is selected from the group consisting of $-O-CH_2-$, $-O-CH_2-CH_2-$, $-O-CH_2-CH_2-CH_2-$, $-O-CH_2-CH_2-CH_2-CH_2-$, $-O-CH_2-CH(CH_2-OH)-(O-CH_2-CH(OH)-CH_2)_2-$, $-O-CH_2-CH_2-CH(CH_2-OH)-(O-CH_2-CH_2-CH(OH)-CH_2)_2-$, $-O-CH_2-CH(OH)-CH_2-$, $-O-CH_2-CH_2-CH(OH)-CH_2-CH_2-$, $-O-CH_2-CH(OH)-CH_2-O-CH_2-CH_2-CH_2-CH_2-O-CH_2-CH(OH)-CH_2-$, and $-CO-NH-C(CH_3)_2-CO-$;
$R^2$ is $C_2$ to $C_4$ alkyl;
L is O;

n=1; and
Ar is a 6 membered ring and:
  if Ar is aryl, the aryl is optionally substituted with up to four $C_1$ to $C_2$ unsubstituted alkyl, $C_3$ or $C_4$ branched alkyl, or fluorine groups; or
  if Ar is heteroaryl, the heteroaryl is optionally substituted with up to three unsubstituted alkyl groups.

In a first aspect of the sixth embodiment, $R^2$ is $C_2$ or $C_3$ alkyl.

In a second aspect of the sixth embodiment, Ar is phenyl, napthyl, or pyridyl optionally substituted with up to three $C_1$ to $C_2$ unsubstituted alkyl or fluorine groups. Alternatively, Ar is phenyl optionally substituted with one or two $C_1$ to $C_2$ unsubstituted alkyl. Alternatively, Ar is phenyl substituted with one $C_1$ or $C_2$ unsubstituted alkyl at the para or meta position relative to —$(R^2$-L$)_n$-. Alternatively, Ar is heteroaryl and a heteroatom in the heteroaryl is N. Alternatively, Ar is unsubstituted heteroaryl. In yet another alternative, Ar is pyridyl.

In a seventh embodiment, the chromatography resin has the formula:

$$\text{Chromatography matrix-(X)}-\text{N}-[(R^2-L)_n-\text{Ar}]_2$$

or an anionic salt thereof,
wherein:
  X is selected from the group consisting of —O—$CH_2$—, —O—$CH_2$—$CH_2$—, —O—$CH_2$—$CH_2$—$CH_2$—, —O—$CH_2$—$CH_2$—$CH_2$—$CH_2$—, and —O—$CH_2$—CH(OH)—$CH_2$—;
  $R^1$ is hydrogen, $C_1$, or $C_2$ alkyl;
  $R^2$ is $C_2$ or $C_3$ alkyl;
  L is O;
  n=1; and
  Ar is phenyl, napthyl, or pyridyl optionally substituted with up to three $C_1$ to $C_2$ unsubstituted alkyl.

In a first aspect of the seventh embodiment, Ar is phenyl optionally substituted with one or two $C_1$ to $C_2$ unsubstituted alkyl. Alternatively, Ar is phenyl substituted with a methyl group at the para or meta position relative to —$(R^2$-L$)_n$-. Alternatively, Ar is unsubstituted phenyl.

In an eighth embodiment, —(X)—N—[$(R^2$-L$)_n$-Ar]$_2$ is any one of the ligands of Table 2.

TABLE 2

| Ligand | Structure of Ligand | Structure of Ligand Attached to Matrix (Spheres represent matrix and Spacer X) |
|---|---|---|
| Bis(2-phenxoyethyl)amine | | |
| Bis[2-(2-phenoxyethoxy)ethyl]amine | | |
| Bis[2-(3,5-xylyloxy)ethyl]amine | | |
| Bis[2-(4-biphenylyloxy)ethyl]amine | | |
| Bis[2-(p-tolyloxy)ethyl]amine | | |

TABLE 2-continued

| Ligand | Structure of Ligand | Structure of Ligand Attached to Matrix (Spheres represent matrix and Spacer X) |
|---|---|---|
| Bis[2-(o-tolyloxy)ethyl]amine | | |
| Bis[2-(m-tolyloxy)ethyl]amine | | |
| Bis[2-(p-ethylphenoxy)ethyl]amine | | |
| Bis[2-(p-cumenyloxy)ethyl]amine | | |
| Bis{2-[p-(tert-butyl)phenoxy]ethyl}amine | | |
| Bis[2-(1-naphthyloxy)ethyl]amine | | |

TABLE 2-continued

| Ligand | Structure of Ligand | Structure of Ligand Attached to Matrix (Spheres represent matrix and Spacer X) |
|---|---|---|
| Bis[2-(p-fluorophenoxy)ethyl]amine | | |
| Bis[2-(2,5-difluorophenoxy)ethyl]amine | | |
| Bis[2-(m-fluorophenoxy)ethyl]amine | | |
| Bis[2-(p-cumenyloxy)ethyl]amine | | |
| Bis[2-(3,4-difluorophenoxy)ethyl]amine | | |
| Bis[2-(3,4,5-trifluorophenoxy)ethyl]amine | | |

TABLE 2-continued

| Ligand | Structure of Ligand | Structure of Ligand Attached to Matrix (Spheres represent matrix and Spacer X) |
|---|---|---|
| Bis[2-(2,3,4,5,6-pentafluorophenoxy)ethyl]amine | | |
| Bis[2-(2,6-dimethyl-4-pyridyloxy)ethyl]amine | | |
| Bis[2-(4-pyridyloxy)ethyl]amine | | |
| Bis[2-(3-pyridyloxy)ethyl]amine | | |
| Bis(3-phenoxycyclobutyl)amine | | |

TABLE 2-continued

| Ligand | Structure of Ligand | Structure of Ligand Attached to Matrix (Spheres represent matrix and Spacer X) |
|---|---|---|
| Bis(3-phenoxycyclopentyl)amine | | |
| Bis(4-phenoxycyclohexyl)amine | | |

In some embodiments, the anionic salt is hydrochloride, phosphate, or sulfate.

The chromatography matrix is a polymer that is functionalized so that a bond can be formed with the spacer, X. Preferably, the polymer is a hydrophilic polymer. The polymer is insoluble in water. Suitable polymers are polyhydroxy polymers, e.g. based on polysaccharides, such as agarose, dextran, cellulose, starch, pullulan, and completely synthetic polymers, such as polyacrylic amide, polymethacrylic amide, poly(hydroxyalkylvinyl ethers), poly(hydroxyalkylacrylates) and polymethacrylates (e.g. polyglycidylmethacrylate), polyvinyl alcohols and polymers based on styrenes and divinylbenzenes, and copolymers in which two or more of the monomers corresponding to the above-mentioned polymers are included. Suitable synthetic polymers include, but are not limited to, Fractogel and Eshmuno® base beads from Sigma-Millipore-EMD-Merck, Toyopearl AF-Eposy-650M and Toyopearl AF-Tresyl-650M from Tosoh Bioscience, POROS media from ThermoFisher Scientific, Bio-Gel P and Macro Prep from Bio-Rad, HEMA and Separon from TESSEK, activated Sepharose 6B, activated Sepharose 4B, and activated Sepharose 4 Fast Flow from GE Healthcare Life Sciences, and Hyper D and Trisacryl media from Pall. Polymers, which are soluble in water, may be derivatized to become insoluble, e.g. by cross-linking and by coupling to an insoluble body via adsorption or covalent binding. Hydrophilic groups can be introduced on hydrophobic polymers (e.g. on copolymers of monovinyl and divinylbenzenes) by polymerisation of monomers exhibiting groups which can be converted to OH, or by hydrophilization of the final polymer, e.g. by adsorption of suitable compounds, such as hydrophilic polymers. Examples of monomers that can be polymerized to achieve useful matrices are vinyl acetate, vinyl propylamine, acrylic acid, methacrylate, butyl acrylate, acrylamide, methacrylamide, vinyl pyrrolidone (vinyl pyrrolidinone), with functional groups in some cases. Cross-linking agents are also of use in many embodiments, and when present can in some embodiments constitute a mole ratio of from about 0.1 to about 0.7 relative to total monomer. Examples of crosslinking agents are dihydroxyethylenebisacrylamide, diallyltartardiamide, triallyl citric triamide, ethylene diacrylate, bisacrylylcystamine, N,N'-methylenebisacrylamide, and piperazine diacrylamide. In some embodiments, the matrix is an UNOsphere™ support, a polymer produced from water-soluble hydrophilic monomers (Bio-Rad, Hercules, Calif.).

The chromatography matrix can be in the form of a particle, chips, a membrane, or a monolith, i.e., a single block, pellet, or slab of material. Preferably, the chromatography matrix is porous. Particles when used as matrices can be spheres or beads and are either smooth-surfaced or with a rough or textured surface. In some cases, some of the pores are through-pores, extending through the particles to serve as channels large enough to permit hydrodynamic flow or fast diffusion through the pores. When in the form of spheres or beads, the median particle diameter, where the term "diameter" refers to the longest exterior dimension of the particle, is about 25 microns to about 150 microns. Disclosures of exemplary matrices and the processes by which they are made are found in Hjertén et al., U.S. Pat. No. 5,645,717, Liao et al., U.S. Pat. No. 5,647,979, Liao et al., U.S. Pat. No. 5,935,429, and Liao et al., U.S. Pat. No. 6,423,666.

The ligands are linked to the chromatography matrix via the spacer X. Linkage to the chromatography matrix will depend on the specific chromatography matrix used and the chemical group to be linked to the chromatography matrix. Ligands can be linked to the chromatography matrix by performing a reaction between the ligand and a functional group on the chromatography matrix. For chromatography matrices that do not have a suitable functional group, the chromatography matrix is reacted with a suitable activating reagent to create a suitable functional group to which the ligand can be attached. Reductive amination, epoxide chemistry or azalactone chemistry are examples of chemistries acting on aldehyde, epoxide, or azalactone functional groups, respectively.

In some embodiments, the chromatography matrix comprises a diol, which is converted to an aldehyde, e.g., by conversion with $NaIO_4$. The primary or secondary amine of the ligand is linked to an aldehyde on the chromatography matrix by a reductive amination reaction by the scheme below. In this scheme, the spacer X is —O—$CH_2$—$CH_2$—$CH_2$—. In this and other synthetic schemes in this disclosure, the square represents the matrix and all coupling chemistry is shown separately.

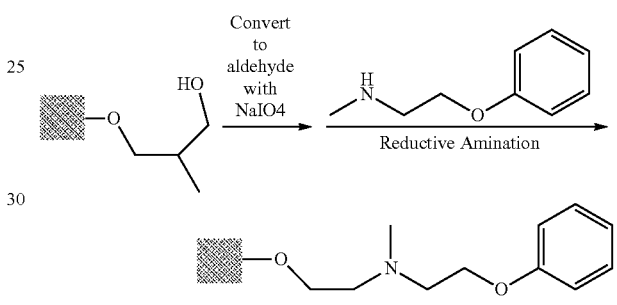

In some embodiments, the chromatography matrix comprises an epoxide group and a primary or secondary amine in the ligand is linked to the epoxide group via epoxide chemistry by the scheme below. In this scheme, the spacer X is —O—$CH_2$—CH(OH)—$CH_2$—.

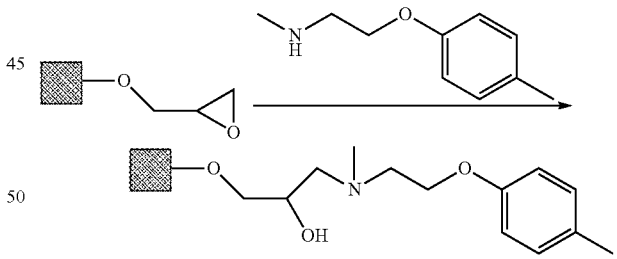

In some embodiments, the chromatography matrix comprises an azlactone ring and a primary or secondary amine in the ligand is linked to the azlactone ring by the scheme below. In this scheme, the spacer X is —CO—NH—C($CH_3$)$_2$—CO—.

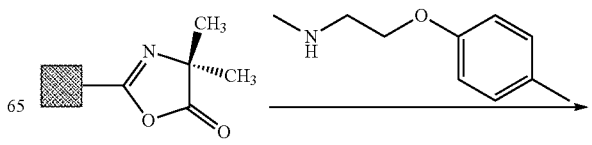

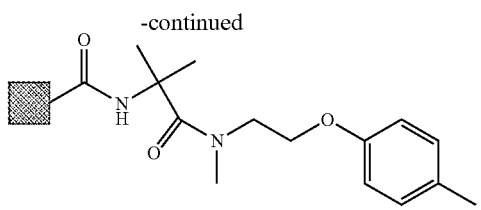

In some embodiments, the chromatography matrix comprises a diol and a primary or a secondary amine is linked to an —OH group by activating the resin with two activating reagents, allylglydicylether (AGE) and bromine, by the scheme below. In this scheme, the spacer X is —O—CH$_2$—CH(CH$_2$—OH)—(O—CH$_2$—CH(OH)—CH$_2$)$_2$—.

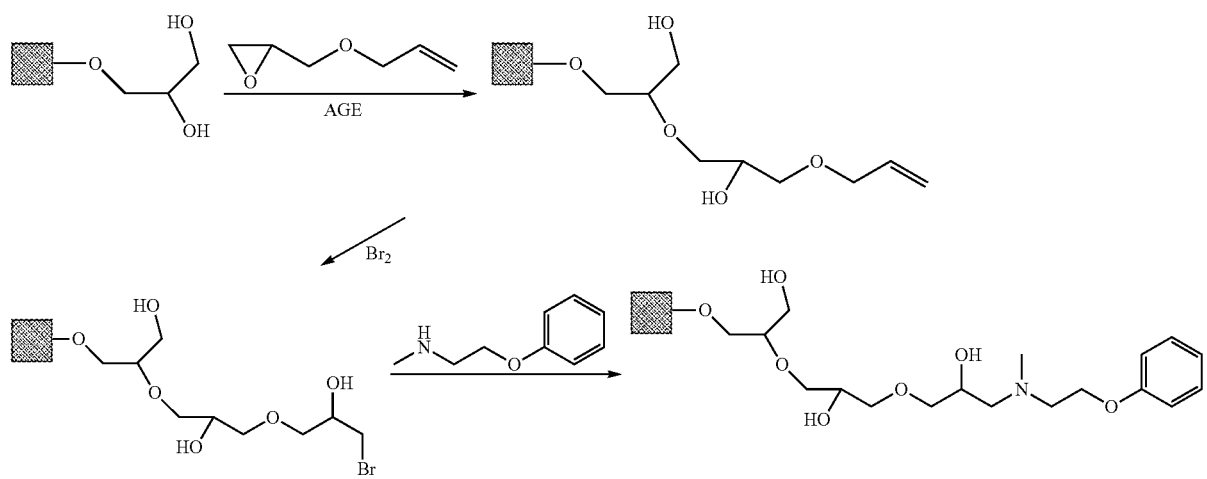

In certain embodiments, the chromatography matrix comprises an —OH group and a primary or secondary amine is linked to the —OH group by activating the resin with epichlorohydrin by the scheme below. In this scheme, the spacer X is —O—CH$_2$—CH(OH)—CH$_2$—.

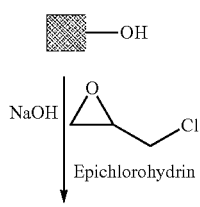

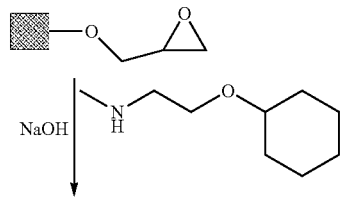

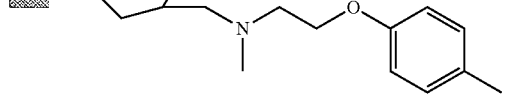

In some embodiments, the chromatography matrix comprises an —OH group and a primary or secondary amine is linked to the —OH group by activating the resin with 1,4 butanedioldiglycidyl ether by the scheme below. In this scheme, the spacer X is —O—CH$_2$—CH(OH)—CH$_2$—O—CH$_2$—CH$_2$—CH$_2$—CH$_2$—O—CH$_2$—CH(OH)—CH$_2$—.

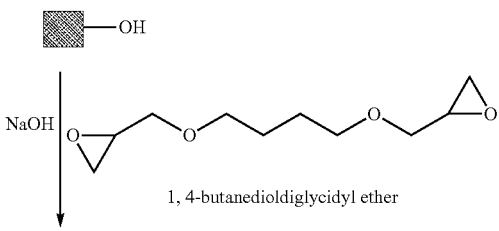

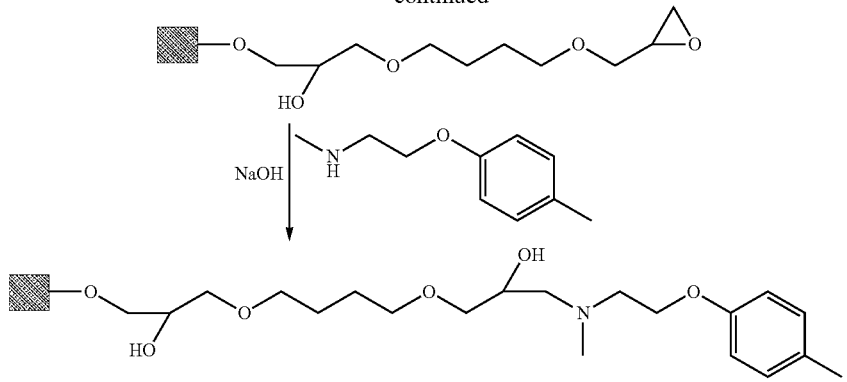

Other activating reagents include, but are not limited to, epibromohydrin (reacts with an —OH functional group on the chromatography matrix to create an epoxide group), poly(ethylene glycol) diglycidyl ether (reacts with an —OH functional group on the chromatography matrix to create an epoxide group), halogen-substituted aliphatic substances such as dichloropropanol (reacts with an —OH functional group on the chromatography matrix to create an epoxide group), divinyl sulfone (reacts with a diol functional group on the chromatography matrix to create a vinyl group), and sulfonyl chlorides such as tosyl chlorides and tresyl chlorides (react with an —OH functional group on the chromatography matrix to create a sulfonate ester).

Other spacers can include, but are not limited to, —O—$CH_2$—, —O—$CH_2$—$CH_2$—, —O—$CH_2$—$CH_2$—$CH_2$—$CH_2$—, —O—$CH_2$—$CH_2$—CH($CH_2$—OH)—(O—$CH_2$—$CH_2$—CH(OH)—$CH_2$)_2—, and —O—$CH_2$—$CH_2$—CH(OH)—$CH_2$—$CH_2$—.

The chromatography matrix can be utilized in any conventional configuration, including packed columns and fluidized or expanded-bed columns, monoliths or porous membranes, and by any conventional method, including batchwise modes for loading, washes, and elution, as well as continuous or flow-through modes. In some embodiments, a column can range in diameter from 1 cm to 1 m, and in height from 1 cm to 30 cm or more.

Methods

Also provided are methods of purifying a target biomolecule. In an embodiment, the method comprises contacting a sample comprising the biomolecule to a chromatography resin, thereby separating the biomolecule from a contaminant. The resulting purified biomolecule is subsequently collected. In some embodiments, the target biomolecule is a target protein and the method comprises purifying the target protein from a contaminant. In some embodiments, the target biomolecule is a monomeric antibody and the method comprises purifying the monomeric antibody from aggregated antibodies in the sample.

The chromatographic ligands are useful for purifying target molecules using anionic exchange (i.e., where the ligand is positively charged) and hydrophobic mixed mode chromatography. The conditions can be adjusted so as to run the chromatography in bind-elute mode or flow-through mode.

Protein preparations to which the methods can be applied can include proteins from natural, synthetic, or recombinant sources. Unpurified protein preparations, for example, can come from various sources including, but not limited to, plasma, serum, ascites fluid, milk, plant extracts, bacterial lysates, yeast lysates, or conditioned cell culture media. Partially purified protein preparations can come from unpurified preparations that have been processed by at least one chromatography, precipitation, other fractionation step, or any combination of the foregoing. In some embodiments, the chromatography step or steps employ any method, including but not limited to size exclusion, affinity, anion exchange, cation exchange, protein A affinity, hydrophobic interaction, immobilized metal affinity chromatography, or hydroxyapatite chromatography. The precipitation step or steps can include salt or polyethylene glycol (PEG) precipitation, or precipitation with organic acids, organic bases, or other agents. Other fractionation steps can include but are not limited to crystallization, liquid:liquid partitioning, or membrane filtration.

As will be appreciated in the art, load, wash and elution conditions for use in the mixed mode chromatography will depend on the specific chromatography media/ligands used.

In some bind-elute mode embodiments, loading (i.e., binding the target protein to the matrix), and optionally washing, is performed at a pH above 6.5, e.g., between 6.5-8, 7-9, etc. Some exemplary bind-elute conditions are:

binding condition: 0-1000 mM NaCl or 0-400 mM NaCl, pH 6.5-8.5 or 7-9 in an appropriate buffer (e.g., Tris, Bis-Tris, sodium phosphate, sodium citrate, or sodium acetate);

elution condition: 10-1000 mM NaCl or 20-500 mM NaCl, pH 3-8.5 or 4-6, using an appropriate buffer having sodium phosphate, sodium acetate, citrate, arginine, or glycine.

Optionally, the matrix can be washed under conditions such that some components of the sample are removed from the chromatography matrix but the target biomolecules remain immobilized on the matrix. In some embodiments, the target biomolecule is subsequently eluted by lowering the salt concentration and/or reducing the pH of the solution in contact with the matrix.

Alternatively, the sample can be applied in flow through mode in which some components of the sample are immobilized to the matrix but the target biomolecules flow through (i.e., flow passed) the chromatography matrix, and is collected. Some exemplary flow through conditions are 0-150 mM NaCl, pH 4.0-8.5; appropriate buffers can include, e.g., 2-(N-morpholino)ethanesulfonic acid (MES), Bis-Tris, sodium acetate or citrate-phosphate.

EXAMPLES

The following examples are provided by way of illustration only and not by way of limitation. Those of skill in the art will readily recognize a variety of non-critical parameters that could be changed or modified to yield essentially the same or similar results.

tration in each of the reactions was determined to be in the range of 25-200 mM. At the end of the reactions, the resins were each transferred to a 20 ml column, washed with 3 CV of water followed by 1-2 CV of 0.1N HCl, and then washed with 5 CV water. The ligand density of each resin was in the range of 25-100 μmol/ml.

The structure and density of the ligands 5, 6, 11, and 16 attached to UNOsphere aldehyde resin are listed in Table 3.

TABLE 3

| Number from TABLE 1 | Structure of Ligand Attached to Matrix (Spheres represent matrix and spacer X) | Ligand Density (micromol/mL) |
| --- | --- | --- |
| 5 | ●—NH—CH₂CH₂—O—C₆H₄—CH₂CH₃ | 86 |
| 6 | ●—NH—CH₂CH₂—O—C₆H₄—CH(CH₃)₂ | 86 |
| 11 | ●—NH—CH₂CH₂—O—C₆H₄—F | 48 |
| 16 | ●—NH—CH₂CH₂—O—C₆F₅ | 56 |

Example 1—Preparation of Chromatography Resins Having the Ligands of Table 2

Primary Amine Ligands 5, 6, 11, and 16 in Table 3:

For each of the primary amine ligands 5, 6, 11, and 16 in Table 3, UNOsphere Diol (20 mL), a copolymer of 3-allyloxy-1,2-propanediol and vinyl pyrrolidinone, crosslinked with N,N'-methylenebisacrylamide and with a diol density of 200-300 μmol/mL, was used in the form of spherical beads. The beads were suspended in 20 mL of either 0.1 M sodium acetate or water. Sodium periodate was added to a concentration within the range of 50 to 100 mM, and the resulting mixture was incubated at room temperature (approximately 70° F. (21° C.)) for 3-24 hours. The reaction resulted in conversion of the diol groups to aldehyde groups in the range of 150-250 μmol/mL. The resulting aldehyde-functionalized resin was transferred to a 20 mL column where it was washed with 100 mL of water.

For each primary amine ligand, twenty milliliters of UNOsphere aldehyde resin was then suspended in 20 ml of 0.20 M sodium phosphate containing 0.6 g of the ligand at pH 7.0. After these mixtures were incubated (shaking, 200 rpm) at room temperature for 15 minutes, 200 mg NaBH₃CN was then added to each mixture and the reaction was allowed to continue for 3-20 hours. The ligand concen- Secondary Amine Ligands 32, 34, 39, and 44 in Table 4:

For each of the secondary amine ligands 32, 34, 39, and 44 in Table 4, UNOsphere Diol (100 mL) was used in the form of spherical beads. The beads were suspended in 30 mL of water, 30 mL ION NaOH and 16 g Na₂SO₄ at 50° C. in a 250 RPM shaker for 10 minutes. 100 mL allylglydicylether (AGE) was added and the mixture was kept at 50° C. in the same shaker overnight. The resulting AGE modified resin was washed with 3×2 column volumes (CV) of isopropyl alcohol (IPA) and 30 CV water. The AGE modified resin was mixed with 100 mL water and 3.4 g NaOAC. Bromine liquid was added drop-wise to the slurry until an orange color remained (indicating the completion of reaction between double bond and bromine). Na₂SO₃ was then added until the orange color disappeared (reduction of excess bromine to bromide). The resulting UNOsphere Diol bromide resin was washed with 30 CV water and was ready for ligand coupling. For each secondary amine ligand, 100 mL UNOsphere Diol bromide resin was mixed with 50 mL water and 50 mL IPA. Then 12.5 g ligand was added. Each mixture was incubated at 50° C. in a 250 RPM shaker overnight. At the end of the reaction, each resin was washed with 2 CV IPA, 2 CV water, 2 CV 1N HCl, 2 CV water, 2 CV 1N NaOH, and then 30 CV water to obtain the resulting tertiary amine resin.

The number, structure, and the density of ligands 32, 34, 39, and 44 attached to UNOsphere Diol bromide resin are listed in Table 4.

TABLE 4

| Number from TABLE 1 | Structure of Ligand Attached to Matrix (Spheres represent matrix and spacer X) | Ligand Density (micromol/mL) |
|---|---|---|
| 33 | ⬤—N—CH₂CH₂—O—C₆H₄—CH₂CH₃ (para-ethyl phenoxy) | 68 |
| 34 | ⬤—N—CH₂CH₂—O—C₆H₄—C(CH₃)₃ (para-tert-butyl phenoxy) | 116 |
| 39 | ⬤—N—CH₂CH₂—O—C₆H₄—F (para-fluoro phenoxy) | 139 |
| 44 | ⬤—N—CH₂CH₂—O—C₆F₅ (pentafluoro phenoxy) | 98 |

Example 2—Evaluation of Amine Resins from Tables 3 and 4 Using Acidic Proteins and Bind-Elute Mode Static binding capacity, recovery, and purity of two model acidic proteins, CDP-D-glucose 4,6-dehydratase and human serum albumin, were determined for the resins from Tables 3 and 4 using various binding and elution conditions.

Materials

1. Resins from Tables 3 and 4.
2. Disposable spin columns (Bio-Rad catalog #732-6207).
3. Crude *E. coli* lysate containing CDP-D-glucose 4,6-dehydratase ("Eod") (pI is about 6; not stable below pH 6).
4. Human serum albumin ("HSA") (Fraction V, Sigma catalog #A1653; pI is about 4.7).
5. Binding/wash buffers for Eod:
   a. 25 mM sodium phosphate buffer at pH 6.5, 7.5, or about 8.5; and
   b. 0, 25, or about 50 mM NaCl.
6. Binding/wash buffers for HSA:
   a. 25 mM sodium phosphate or sodium acetate buffer at pH 4, 6, or about 8; and
   b. 0, 200, or about 400 mM NaCl.
7. Elution buffers for Eod:
   a. 25 mM sodium phosphate buffer at pH 6.5, 7.5, or about 8.5; and
   b. 10, 500, or about 1000 mM NaCl.
8. Elution buffers for HSA:
   a. 25 mM sodium phosphate or sodium acetate buffer at pH 4, 6, or about 8; and
   b. 20, 500, or about 1000 mM NaCl.

Methods

Static binding capacity (SBC) determination: For each resin and target protein tested (i.e., Eod and/or HSA), a spin column containing 0.1 ml of resin was pre-equilibrated with an appropriate binding buffer (depending on the target protein) and then was incubated with Eod-containing lysate or an HSA solution for 5 min. For each resin and target protein, the binding/wash buffer at three different pH values (e.g., pH 6.5, 7.5, 8.5 for Eod) in combination with three different NaCl concentrations (e.g., 0, 25, 50 mM NaCl for Eod) was tested with each of three elution buffer pH and NaCl concentration combinations. Thus, each resin and target protein was tested with 9 binding/wash buffer combinations and each of the binding/wash buffer combinations was tested with 9 elution buffer combinations.

The columns were centrifuged at 1000×g for 1 minute to remove unbound proteins/impurities, washed once with 5 column volumes of the appropriate binding/wash buffer, and then incubated with 5 CV of an appropriate elution buffer (depending on the target protein) to recover bound target protein. The columns were centrifuged again at 1000×g for 1 minute and the column effluent absorbance at 280 nm was determined along with the absorbance at 280 nm of the original protein solution loaded onto the spin column. Static binding capacity was determined by the following equation:

$$SBC = $$

(total protein loaded − protein in flow−through fraction)/volume of resin.

Target protein recovery: For each resin, the protein recovered in the eluate was quantified by absorbance at 280 nm, an extinction coefficient of 1 for Eod and 0.534 for HSA (for a 1 mg/mL solution of the target protein), and the following equation:

$$\text{Recovery (\%)} = (\text{Total protein in eluate/Total loaded protein}) \times 100.$$

Target protein purity: The purity of the target protein for each resin was assessed by SDS-PAGE and Bio-Rad's ImageLab software.

Optimal binding and elution conditions: JMP software (SAS Institute) was used to determine optimal purification conditions with each target protein and resin.

Results: The results for SBC, recovery for the resins are tabulated in Table 5 (secondary amine resins 5, 6, 11, and 16) and Table 6 (tertiary amine resins 32, 34, 39, and 44). Tables 5 and 6 also list the optimal binding and elution condition for each resin. In Table 5, "~" symbolizes "to about" and in both tables, [NaCl] refers to NaCl concentration.

TABLE 5

Results for Secondary Amine Resins

| Resin Number | Test Protein | SBC (mg/mL) | Recovery (%) | Purity (A) | Optimal Binding Condition | Optimal Elution Condition |
|---|---|---|---|---|---|---|
| 5 | Eod | 10-14 | 7-100 | 29-100 | pH 6.5, [NaCl] = 0 mM | pH 8.5, [NaCl] = 1000 mM |
| 6 | Eod | | Not eluted at any pH or salt concentration | | | |
|   | HSA | 1~11 | 46~69 | 18~98 | pH 8.0, [NaCl] = 400 mM | pH 8.0, [NaCl] = 1000 mM |
| 11 | Eod | 12~15 | 22-100 | 28-97 | pH 6.5, [NaCl] = 0 mM | pH 8.5, [NaCl] = 1000 mM |
| 16 | Eod | 14-45 | 14-100 | 27-100 | pH 8.5, [NaCl] = 50 mM | pH 8.5, [NaCl] = 1000 mM |

TABLE 6

Results for Tertiary Amine Resins

| Resin Number | Test Protein | SBC (mg/mL) | Recovery (%) | Purity (A) | Optimal Binding Condition | Optimal Elution Condition |
|---|---|---|---|---|---|---|
| 32 | Eod | 29-49 | 1-22 | 29-100 | pH 8.5, [NaCl] = 0 mM | pH 8.5, [NaCl] = 1000 mM |
|    | HSA | 68-76 | 66-98 | 22-97 | pH 8.0, [NaCl] = 0 mM | pH 4.0, [NaCl] = 1000 mM |
| 34 | HSA | 12-36 | 5-9 | 1-100 | pH 4.0, [NaCl] = 0 mM | pH 4.0, [NaCl] = 1000 mM |
| 39 | HSA | 3-9 | 41-100 | 8-88 | pH 8.0, [NaCl] = 0 mM | pH 4.0, [NaCl] = 1000 mM |
| 44 | HSA | 18-52 | 3-34 | 25-89 | pH 8.0, [NaCl] = 0 mM | pH 4.0, [NaCl] = 20 mM |

The data from Tables 5 and 6 show a range of optimal binding and elution conditions that depended on the target protein and the resin. For example, for Eod as the target protein, the optimal binding condition was pH 6.5/no NaCl when tested with resin 5, whereas the optimal binding condition was pH 8.5/50 mM NaCl for resin 16. Similarly, for HSA as the target protein, the optimal binding condition was pH 8.0/400 mM NaCl with resin 6, whereas the optimal binding condition was pH 4.0/no NaCl for resin 34.

The optimum elution condition for resins 5, 11, and 16 tested with Eod as the target protein, was high pH (8-8.5) and high NaCl concentration (1000 mM). However, for resin 44 tested with HSA, the optimum elution condition was low pH (4) and low NaCl concentration (20 mM).

The data from Tables 5 and 6 indicate that the resins can be used at a wide range of pH values and NaCl concentrations and that selection of the resin for a given application will depend on the target protein of interest.

All patents, patent applications, and other published reference materials cited in this specification are hereby incorporated herein by reference in their entirety.

Additional Disclosure and Claimable Subject Matter

Item 1. A chromatography matrix covalently linked to a ligand having the following formula:

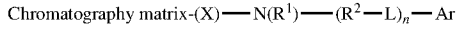

Chromatography matrix-(X)—N($R^1$)—($R^2$—L)$_n$—Ar or an anionic salt thereof,
wherein:
   X is a spacer;
   $R^1$ is hydrogen or $C_1$ to $C_6$ alkyl optionally substituted with an —OH;
   $R^2$ is $C_2$ to $C_6$ alkyl or $C_4$ to $C_6$ cycloalkyl;
   L is $NR^4$, O, or S;
   n=1 or 2; and
   Ar is a 6-10 membered ring and:

if Ar is aryl, the aryl is optionally substituted with up to five $C_1$ to $C_3$ unsubstituted alkyl, $C_3$ to $C_6$ branched alkyl, unsubstituted aryl, or fluorine groups; or if Ar is heteroaryl, the heteroaryl is optionally substituted with up to four unsubstituted alkyl groups, with the proviso that when $R^1$ is hydrogen, $R^2$ is $C_2$ alkyl, L is $NR^4$ or O, and n is 1, Ar is not phenyl.

Item 2. The chromatography matrix of item 1, wherein:
X is selected from the group consisting of —O—$CH_2$—, —O—$CH_2$—$CH_2$—, —O—$CH_2$—$CH_2$—$CH_2$—, —O—$CH_2$—$CH_2$—$CH_2$—$CH_2$—, —O—$CH_2$—CH($CH_2$—OH)—(O—$CH_2$—CH(OH)—$CH_2$)$_2$—, —O—$CH_2$—$CH_2$—CH($CH_2$—OH)—(O—$CH_2$—$CH_2$—CH(OH)—$CH_2$)$_2$—, —O—$CH_2$—CH(OH)—$CH_2$—, —O—$CH_2$—$CH_2$—CH(OH)—$CH_2$—$CH_2$—, —O—$CH_2$—CH(OH)—$CH_2$—O—$CH_2$—$CH_2$—$CH_2$—$CH_2$—O—$CH_2$—CH(OH)—$CH_2$—, and —CO—NH—C($CH_3$)$_2$—CO—;
$R^1$ is hydrogen or $C_1$ to $C_3$ alkyl;
$R^2$ is $C_2$ to $C_4$ alkyl;
L is O;
n=1; and
Ar is a 6 membered ring and:
  if Ar is aryl, the aryl is optionally substituted with up to four $C_1$ to $C_2$ unsubstituted alkyl, $C_3$ or $C_4$ branched alkyl, or fluorine groups; or
  if Ar is heteroaryl, the heteroaryl is optionally substituted with up to three unsubstituted alkyl groups, with the proviso that when $R^1$ is hydrogen, $R^2$ is $C_2$ alkyl, and n is 1, Ar is not phenyl.

Item 3. The chromatography matrix of item 2, wherein:
X is selected from the group consisting of —O—$CH_2$—, —O—$CH_2$—$CH_2$—, —O—$CH_2$—$CH_2$—$CH_2$—, —O—$CH_2$—$CH_2$—$CH_2$—$CH_2$—, and —O—$CH_2$—CH(OH)—$CH_2$—;
$R^1$ is hydrogen or $C_1$ to $C_2$ alkyl;
$R^2$ is $C_2$ to $C_3$ alkyl;
L is O;
n=1; and
Ar is phenyl, napthyl, or pyridyl optionally substituted with up to three $C_1$ to $C_2$ unsubstituted alkyl, with the proviso that when $R^1$ is hydrogen, $R^2$ is $C_2$ alkyl, and n is 1, Ar is not phenyl.

Item 4. The chromatography resin of any one of items 1-3, wherein Ar is phenyl substituted with one or two $C_1$ to $C_2$ unsubstituted alkyl at the para or meta position relative to Chromatography matrix —(X)—$N(R^1)$—$(R^2\text{-L})_n$-.

Item 5. The chromatography resin of any one of items 1-4, wherein —(X)—$N(R^1)$—$(R^2\text{-L})_n$-Ar is any one of the ligands of Table 1.

Item 6. A chromatography resin having the following formula:

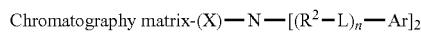

Chromatography matrix-(X)—N—$[(R^2-L)_n—Ar]_2$ or an anionic salt thereof,
wherein:
X is a spacer;
$R^2$ is $C_2$ to $C_6$ alkyl or $C_4$ to $C_6$ cycloalkyl;
L is $NR^4$, O, or S;
n=1 or 2; and
Ar is a 6-10 membered ring and:

if Ar is aryl, the aryl is optionally substituted with up to five $C_1$ to $C_3$ unsubstituted alkyl, $C_3$ to $C_6$ branched alkyl, unsubstituted aryl, or fluorine groups; or if Ar is heteroaryl, the heteroaryl is optionally substituted with up to four unsubstituted alkyl groups.

Item 7. The chromatography matrix of item 6, wherein:
X is selected from the group consisting of —O—$CH_2$—, —O—$CH_2$—$CH_2$—, —O—$CH_2$—$CH_2$—$CH_2$—, —O—$CH_2$—$CH_2$—$CH_2$—$CH_2$—, —O—$CH_2$—CH($CH_2$—OH)—(O—$CH_2$—CH(OH)—$CH_2$)$_2$—, —O—$CH_2$—$CH_2$—CH($CH_2$—OH)—(O—$CH_2$—$CH_2$—CH(OH)—$CH_2$)$_2$—, —O—$CH_2$—CH(OH)—$CH_2$—, —O—$CH_2$—$CH_2$—CH(OH)—$CH_2$—$CH_2$—, —O—$CH_2$—CH(OH)—$CH_2$—O—$CH_2$—$CH_2$—$CH_2$—$CH_2$—O—$CH_2$—CH(OH)—$CH_2$—, and —CO—NH—C($CH_3$)$_2$—CO—;
$R^2$ is $C_2$ to $C_4$ alkyl;
L is O;
n=1; and
Ar is a 6 membered ring and:
  if Ar is aryl, the aryl is optionally substituted with up to four $C_1$ to $C_2$ unsubstituted alkyl, $C_3$ or $C_4$ branched alkyl, or fluorine groups; or
  if Ar is heteroaryl, the heteroaryl is optionally substituted with up to three unsubstituted alkyl groups.

Item 8. The chromatography matrix of item 7, wherein:
X is selected from the group consisting of —O—$CH_2$—, —O—$CH_2$—$CH_2$—, —O—$CH_2$—$CH_2$—$CH_2$—, —O—$CH_2$—$CH_2$—$CH_2$—$CH_2$—, and —O—$CH_2$—CH(OH)—$CH_2$—;
$R^1$ is hydrogen, $C_1$, or $C_2$ alkyl;
$R^2$ is $C_2$ or $C_3$ alkyl;
L is O;
n=1; and
Ar is phenyl, napthyl, or pyridyl optionally substituted with up to three $C_1$ to $C_2$ unsubstituted alkyl.

Item 9. The chromatography resin of any one of items 6-8, wherein Ar is phenyl substituted with one or two $C_1$ to $C_2$ unsubstituted alkyl at the para or meta position relative to —$(R^2\text{-L})_n$-.

Item 10. The chromatography resin of any one of items 6-9, wherein —(X)—N—$[(R^2\text{-L})_n\text{-Ar}]_2$ is any one of the ligands of Table 2.

Item 11. The chromatography resin of item 1 or 6, wherein Ar is heteroaryl and a heteroatom in the heteroaryl is N.

Item 12. The chromatography resin of any one of items 1-11, wherein the anionic salt is a hydrochloride salt, a phosphate salt, or a sulfate salt.

Item 13. The chromatography resin of any one of items 1-12, wherein X is attached to chromatography matrix via an amine, ether or amide bond.

Item 14. A chromatography resin prepared by reacting any one of the ligands of Table 1 with a chromatography matrix by any one of reductive amination, epoxide chemistry, or azalactone chemistry.

Item 15. The chromatography resin of item 14, wherein the chromatography matrix comprises an aldehyde group and any one of the ligands of Table 1 is reacted with the chromatography matrix by reductive amination.

Item 16. The chromatography resin of item 14, wherein the chromatography matrix comprises an epoxide group and any one of the ligands of Table 1 is reacted with the chromatography matrix by epoxide chemistry.

Item 17. The chromatography resin of any one of items 14-16 wherein prior to reacting the chromatography matrix with the ligand, the chromatography matrix is reacted with allylglydicylether and bromine; 1,4-butanedioldiglycidyl; or epichlorohydrin.

Item 18. A chromatography resin prepared by reacting any one of the ligands of Table 2 with a chromatography matrix by epoxide chemistry.

Item 19. A method of purifying a biomolecule, the method comprising: contacting a sample comprising the biomolecule to a chromatography resin of any one of items 1-18, thereby separating the biomolecule from a contaminant; and collecting a purified biomolecule.

Item 20. The method of item 19, wherein the purified biomolecule is a protein.

Item 21. The method of item 20, wherein the contacting step comprises immobilizing the protein to the chromatography matrix and the collecting step comprises eluting the protein from the chromatography matrix.

Item 22. The method of item 21, wherein the protein is eluted by a step comprising reducing a pH of a solution in contact with the ligand from about 7-9 to about 4-6.

Item 23. The method of item 20, wherein the contacting step comprises flowing the protein through the chromatography matrix and the collecting step comprises collecting the protein in the flow through.

The invention claimed is:

1. A chromatography resin having the following formula:

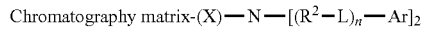

Chromatography matrix-(X)—N—[($R^2$—L)$_n$—Ar]$_2$ or an anionic salt thereof,
wherein:
X is a spacer;
$R^2$ is $C_2$ to $C_6$ alkyl or $C_4$ to $C_6$ cycloalkyl;
L is $NR^4$, O, or S;
n=1 or 2; and
Ar is a 6-10 membered ring and:
  if Ar is aryl, the aryl is optionally substituted with up to five $C_1$ to $C_3$ unsubstituted alkyl, $C_3$ to $C_6$ branched alkyl, unsubstituted aryl, or fluorine groups; or
  if Ar is heteroaryl, the heteroaryl is optionally substituted with up to four unsubstituted alkyl groups.

2. The chromatography matrix of claim 1, wherein:
X is selected from the group consisting of —O—$CH_2$—, —O—$CH_2$—$CH_2$—, —O—$CH_2$—$CH_2$—$CH_2$—, —O—$CH_2$—$CH_2$—$CH_2$—$CH_2$—, —O—$CH_2$—CH($CH_2$—OH)—(O—$CH_2$—CH(OH)—$CH_2$)$_2$—, —O—$CH_2$—$CH_2$—CH($CH_2$—OH)—(O—$CH_2$—$CH_2$—CH(OH)—$CH_2$)$_2$—, —O—$CH_2$—CH(OH)—$CH_2$—, —O—$CH_2$—$CH_2$—CH(OH)—$CH_2$—$CH_2$—, —O—$CH_2$—CH(OH)—$CH_2$—O—$CH_2$—$CH_2$—$CH_2$—$CH_2$—O—$CH_2$—CH(OH)—$CH_2$—, and —CO—NH—C($CH_3$)$_2$—CO—;
$R^2$ is $C_2$ to $C_4$ alkyl;
L is O;
n=1; and
Ar is a 6 membered ring and:
  if Ar is aryl, the aryl is optionally substituted with up to four $C_1$ to $C_2$ unsubstituted alkyl, $C_3$ or $C_4$ branched alkyl, or fluorine groups; or
  if Ar is heteroaryl, the heteroaryl is optionally substituted with up to three unsubstituted alkyl groups.

3. The chromatography matrix of claim 2, wherein:
X is selected from the group consisting of —O—$CH_2$—, —O—$CH_2$—$CH_2$—, —O—$CH_2$—$CH_2$—$CH_2$—, —O—$CH_2$—$CH_2$—$CH_2$—$CH_2$—, and —O—$CH_2$—CH(OH)—$CH_2$—;
$R^1$ is hydrogen, $C_1$ or $C_2$ alkyl;
$R^2$ is $C_2$ or $C_3$ alkyl;
L is O;
n=1; and
Ar is phenyl, napthyl, or pyridyl optionally substituted with up to three $C_1$ to $C_2$ unsubstituted alkyl.

4. The chromatography resin of claim 1, wherein Ar is phenyl substituted with one or two $C_1$ to $C_2$ unsubstituted alkyl at the para or meta position relative to —($R^2$-L)$_n$-.

5. The chromatography resin of claim 1, wherein —[($R^2$-L)$_n$-Ar]$_2$ is selected from the group consisting of:
bis(2-phenoxyethyl)amine;
bis[2-(2-phenoxyethoxy)ethyl]amine;
bis[2-(3,5-xylyloxy)ethyl]amine;
bis[2-(4-biphenylyloxy)ethyl]amine;
bis[2-(p-tolyloxy)ethyl]amine;
bis[2-(o-tolyloxy)ethyl]amine;
bis[2-(m-tolyloxy)ethyl]amine;
bis[2-(p-ethylphenoxy)ethyl]amine;
bis[2-(p-cumenyloxy)ethyl]amine;
bis{2-[p-(tert-butyl)phenoxy]ethy}amine;
bis[2-(1-naphthyloxy)ethyl]amine;
bis[2-(p-fluorophenoxy)ethyl]amine;
bis[2-(2,5-difluorophenoxy)ethyl]amine;
bis[2-(m-fluorophenoxy)ethyl]amine;
bis[2-(p-cumenyloxy)ethyl]amine;
bis[2-(3,4-difluorophenoxy)ethyl]amine;
bis[2-(3,4,5-trifluorophenoxy)ethyl]amine;
bis[2-(2,3,4,5,6-pentafluorophenoxy)ethyl]amine;
bis[2-(2,6-dimethyl-4-pyridyloxy)ethyl]amine;
bis[2-(4-pyridyloxy)ethyl]amine;
bis[2-(3-pyridyloxy)ethyl]amine;
bis(3-phenoxycyclobutyl)amine;
bis(3-phenoxycyclopentyl)amine; and
bis(4-phenoxycyclohexyl)amine.

6. A chromatography resin prepared by reacting a ligand with a chromatography support comprising an aldehyde group, epoxide group, or an azalactone group, wherein the ligand is selected from the group consisting of:
bis(2-phenoxyethyl)amine;
bis[2-(2-phenoxyethoxy)ethyl]amine;
bis[2-(3,5-xylyloxy)ethyl]amine;
bis[2-(4-biphenylyloxy)ethyl]amine;
bis[2-(p-tolyloxy)ethyl]amine;
bis[2-(o-tolyloxy)ethyl]amine;
bis[2-(m-tolyloxy)ethyl]amine;
bis[2-(p-ethylphenoxy)ethyl]amine;
bis[2-(p-cumenyloxy)ethyl]amine;
bis{2-[p-(tert-butyl)phenoxy]ethyl}amine;
bis[2-(1-naphthyloxy)ethyl]amine;
bis[2-(p-fluorophenoxy)ethyl]amine;
bis[2-(2,5-difluorophenoxy)ethyl]amine;
bis[2-(m-fluorophenoxy)ethyl]amine;
bis[2-(p-cumenyloxy)ethyl]amine;
bis[2-(3,4-difluorophenoxy)ethyl]amine;
bis[2-(3,4,5-trifluorophenoxy)ethyl]amine;
bis[2-(2,3,4,5,6-pentafluorophenoxy)ethyl]amine;
bis[2-(2,6-dimethyl-4-pyridyloxy)ethyl]amine;
bis[2-(4-pyridyloxy)ethyl]amine;

bis[2-(3-pyridyloxy)ethyl]amine;
bis(3-phenoxycyclobutyl)amine;
bis(3-phenoxycyclopentyl)amine; and
bis(4-phenoxycyclohexyl)amine.

* * * * *